(12) United States Patent
Dasgupta et al.

(10) Patent No.: US 7,367,945 B2
(45) Date of Patent: May 6, 2008

(54) ULTRASOUND SYSTEM

(75) Inventors: Samhita Dasgupta, Niskayuna, NY (US); Matthew Christian Nielsen, Scotia, NY (US); Min-Yi Shih, Niskayuna, NY (US); Robert John Filkins, Niskayuna, NY (US); Todd Ryan Tolliver, Clifton Park, NY (US); Bruno Hans Haider, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 247 days.

(21) Appl. No.: 10/812,243

(22) Filed: Mar. 29, 2004

(65) Prior Publication Data
US 2005/0215894 A1 Sep. 29, 2005

(51) Int. Cl.
*A61B 8/00* (2006.01)
(52) U.S. Cl. .................................... 600/443
(58) Field of Classification Search ............... 600/437, 600/443–447; 310/334, 357–359; 73/625–626; 359/1, 237–238, 245, 275–276, 278, 305, 359/310–315
See application file for complete search history.

(56) References Cited

U.S. PATENT DOCUMENTS

| 4,739,521 | A | * | 4/1988 | Akimoto |
|---|---|---|---|---|
| 4,923,288 | A | * | 5/1990 | Allen et al. .................. 359/276 |
| 5,010,346 | A | * | 4/1991 | Hamilton et al. |
| 5,081,993 | A | * | 1/1992 | Kitney et al. |
| 5,125,410 | A | * | 6/1992 | Misono et al. ............... 600/463 |
| 5,353,262 | A | * | 10/1994 | Yakymyshyn et al. |
| 5,396,362 | A | * | 3/1995 | Yakymyshyn et al. ...... 359/245 |
| 5,419,329 | A | * | 5/1995 | Smith et al. ................. 600/447 |
| 5,532,981 | A | * | 7/1996 | Duggal et al. |
| 5,565,867 | A | * | 10/1996 | Tiemann ...................... 341/143 |
| 5,566,133 | A | | 10/1996 | Engeler et al. |
| 5,715,823 | A | * | 2/1998 | Wood et al. |
| 5,718,226 | A | * | 2/1998 | Riza |
| 5,739,936 | A | * | 4/1998 | Yakymyshyn et al. ...... 398/145 |
| 5,949,491 | A | * | 9/1999 | Callahan et al. |
| 6,101,407 | A | * | 8/2000 | Groezinger |

(Continued)

FOREIGN PATENT DOCUMENTS

EP        0 763 192 B1        3/1997

(Continued)

OTHER PUBLICATIONS

U.S. Appl. No. 10/436,929 filed May 12, 2003, Entitled "Crosslinked Polymers" By James A. Cella, et al.

(Continued)

*Primary Examiner*—Francis J. Jaworski
(74) *Attorney, Agent, or Firm*—Ann M. Agosti; Patrick K. Patnode

(57) ABSTRACT

An ultrasound system includes an ultrasound probe configured for sensing and transmitting ultrasound signals. The ultrasound system further includes an optical conduit configured for coupling a light source and an optical detector in an optical path. The optical conduit includes electro-optic modulators configured for modulating optical signals on the optical conduit with at least one of the electrical signals configured to generate corresponding optically modulated analog signals on the optical conduit. In one example, the electro-optic modulators comprise electro-optic polymer modulators.

12 Claims, 6 Drawing Sheets

U.S. PATENT DOCUMENTS

| | | | |
|---|---|---|---|
| 6,118,397 A * | 9/2000 | Heflinger | 341/137 |
| 6,139,497 A | 10/2000 | Amemiya et al. | |
| 6,142,946 A * | 11/2000 | Hwang et al. | |
| 6,248,069 B1 * | 6/2001 | Liu et al. | 600/437 |
| 6,476,541 B1 * | 11/2002 | Smith et al. | 310/334 |
| 6,529,150 B1 * | 3/2003 | Shoop et al. | |
| 6,569,097 B1 * | 5/2003 | McMorrow et al. | |
| 6,609,425 B2 * | 8/2003 | Ogawa | 73/608 |
| 6,783,494 B2 * | 8/2004 | Ogawa | 600/437 |
| 6,890,301 B2 * | 5/2005 | Jago et al. | |

FOREIGN PATENT DOCUMENTS

| | | |
|---|---|---|
| EP | 0762142 A1 * | 3/1997 |
| EP | 0762142 A1 * | 12/1997 |
| JP | 56157879 * | 12/1981 |
| JP | 61296266 * | 12/1986 |

OTHER PUBLICATIONS

U.S. Appl. No. 10/437,278, filed May 12, 2003, Entitled "Thermally Crosslinked Polymers" By James A Cella, et al.

* cited by examiner

ULTRASOUND SYSTEM

BACKGROUND OF THE INVENTION

The invention relates generally to ultrasound systems, and more specifically to a method and system for design of an ultrasound probe using fiber optics.

Conventional ultrasound scanners comprise an ultrasound probe for transmitting ultrasound signals to an area to be examined as well as for receiving scattered waves. The ultrasound probe usually comprises several transducer elements that are configured for sensing the backscattered waves.

The transducer elements convert the backscattered waves to corresponding electrical signals. The electrical signals are transmitted to a processing unit where the electrical signals are processed to generate a corresponding image of the area that was scanned.

Typically, the electrical signals are transferred to the processing unit by cables. While designing the ultrasound probe, it is desirable to maintain the diameter of the probe cable at a size that is maneuverable by an operator.

It is often desirable to obtain a high resolution for the image generated by the ultrasound system. One way to increase the resolution is to increase the number of transducer elements in the ultrasound probe. One problem with increasing the number of transducer elements is the increase in the cable diameter. An increase in the cable diameter results in restrictive maneuverability of the ultrasound probe.

Another problem with conventional ultrasound system is the short cable length. In order it maintain signal integrity, the length of the cable is limited. Thus, the mobility of the ultrasound scanner is restricted to a large extent.

In addition, the transducer elements, when operating, generate substantial amounts of heat. The heat generated may cause inconvenience to an operator who is using the ultrasound probe.

It is therefore desirable to increase sensitivity of the ultrasound probe while maintaining the diameter of the probe and also maintain the probe temperature at a desired level. It is also desirable to increase the length of the probe cable to provide better mobility.

BRIEF DESCRIPTION OF THE INVENTION

Briefly, in accordance with one embodiment of the invention, an ultrasound system is provided. The ultrasound system comprises an ultrasound probe configured for sensing and transmitting analog electrical signal. The ultrasound system further comprises an optical conduit configured for coupling a light source and a optical detector in an optical path; wherein the optical conduit comprises electro-optic modulators configured for modulating optical signals on the optical conduit with at least one of the electrical signals configured to generate corresponding optically modulated analog signals on the optical conduit.

According to another aspect of the invention, a method for generating an image is provided. The method comprises sensing a plurality of ultrasound signals and generating corresponding electrical signals and modulating the optical signals with the electrical signals to generate a corresponding plurality of optically modulated analog signals. The method further comprises converting the plurality of optically modulated analog signals to a corresponding plurality of digital signals and processing the plurality of digital signals to generate the image.

In an alternate embodiment, the ultrasound system comprises an ultrasound probe configured for sensing and transmitting analog electrical signals and a optical conduit configured for coupling a light source and an optical detector in an optical path through the ultrasound probe. The ultrasound system further comprises electro-optic polymer modulators configured for modulating optical signals on the optical conduit with at least one of the analog electrical signals to generate corresponding optically modulated analog signals on the optical conduit.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
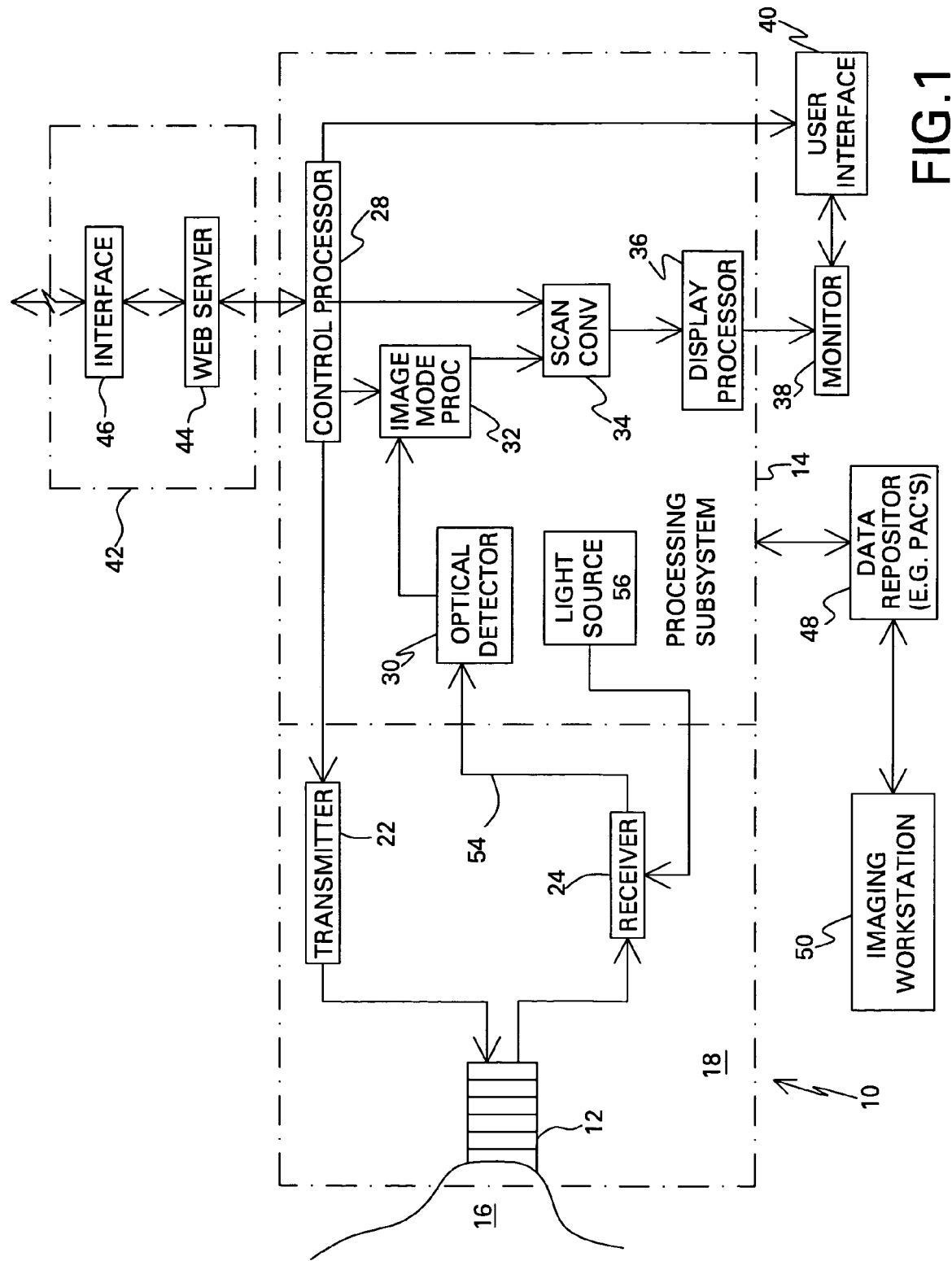
FIG. 1 is a block diagram illustrating an exemplary ultrasound system implemented according to one aspect of the invention.

In one embodiment of the present invention, an ultrasound system 10 for generating an image is provided as shown in FIG. 1. The ultrasound system comprises an ultrasound probe 18 configured for sensing ultrasound signals and transmitting electrical signals representative of the sensed ultrasound signals. The ultrasound probe comprises transducer array 12, transmitter 22, and receiver 24. The electrical signals are transmitted to optical detector 30 via optical conduit 54. The optical conduit 54 (illustrated in FIG. 2) configured for coupling a light source and an optical detector 30 in an optical path. The optical conduit comprises electro-optic modulators configured for modulating optical signals on the optical conduit with at least one of the ultrasound signals to generate corresponding optically modulated analog signals on the optical conduit. The optical conduit is described in detail with reference to FIG. 2. The ultrasound probe is described in detail with reference to FIG. 4.

In one more specific aspect of the present invention, the ultrasound signals transmitted by the ultrasound probe comprise analog electrical signals. In another more specific aspect of the present invention, which may be used in combination or separately from the analog electrical signal aspect, the electro-optic modulators comprise electro-optic polymer modulators. This aspect is advantageous because electro-optic polymer devices are compact, and flexible and can be densely packed to fit a head of a probe. In addition, electro-optic polymer devices consume lower power.

Referring to FIG. 1 is a block diagram of an illustrative, more specific embodiment of an ultrasound system 10 implemented in accordance to one aspect of the invention. The ultrasound system comprises an ultrasound probe 12 a transmitter 22 and a receiver 24. The ultrasound system further comprises a processing subsystem 14 comprising a control processor 28, an optical detector 30, an imaging mode processor 32, a scan converter 34 and a display processor 36. The display processor is further coupled to a monitor for displaying images. User interface 40 interacts with the control processor and the display monitor. The control processor may also be coupled to a remote connectivity subsystem 42 comprising a web server 44 and a remote connectivity interface 46. Processing subsystem may be further coupled to data repository 48 to receive ultrasound image data. The data repository interacts with image workstation 50.

The architectures and modules may be dedicated hardware elements such as circuit boards with digital signal processors or may be software running on a general purpose computer or processor such as a commercial, off-the-shelf PC. The various architectures and modules may be combined or separated according to various embodiments of the invention.

As illustrated in FIG. 1, the ultrasound probe 12 is in contact with subject 16. The ultrasound probe is coupled to the output of transmitter 22 and the input of receiver 24. In processing subsystem 14, the output of optical detector 30 is coupled to an input of imaging mode processor 32. Control processor interfaces to imaging mode processor 32, scan converter 34 and to display processor 36. An output of imaging mode processor 32 is coupled to an input of scan converter 34. An output of scan converter 34 is coupled to an input of display processor 36. The output of display processor 36 is coupled to monitor 38.

Ultrasound system 10 transmits ultrasound energy into subject 16 and receives and processes backscattered ultrasound signals from the subject to create and display an image. To generate a transmitted beam of ultrasound energy, the control processor 28 sends command data to the transmitter 22 to generate transmit parameters to create a beam of a desired shape originating from a certain point at the surface of the ultrasound probe 12 at a desired steering angle.

The transmitter 22 uses the transmit parameters to properly encode transmit signals to be sent to the ultrasound probe 12. The transmit signals are set at certain levels and phases with respect to each other and are provided to individual transducer elements of the ultrasound probe 12. The transmit signals excite the transducer elements to emit ultrasound waves with the same phase and level relationships. As a result, a transmitted beam of ultrasound energy is formed in a subject within a scan plane along a scan line when the ultrasound probe 12 is acoustically coupled to the subject by using, for example, ultrasound gel. The process is known as electronic scanning.

The ultrasound probe 12 is a two-way transducer. When ultrasound waves are transmitted into a subject, the ultrasound waves are backscattered off the tissue and blood samples within the structure. The ultrasound probe 12 receives the backscattered waves at different times, depending on the distance into the tissue they return from and the angle with respect to the surface of the ultrasound probe 12 at which they return. In one embodiment, the transducer elements are configured for sensing the backscattered waves and converting the ultrasound signals to corresponding analog electrical signals.

The received electrical signals are routed through receiver 24 to the processing subsystem 14. Optical detector 30 coverts the optically modulated analog signals received from receiver 24 to electrical signals. The electrical signals are transferred to imaging mode processor 32. Imaging mode processor 32 uses parameter estimation techniques to generate imaging parameter values from the demodulated data in scan sequence format. The imaging parameters may comprise parameters corresponding to various possible imaging modes such as, for example, B-mode, color velocity mode, spectral Doppler mode, and tissue velocity imaging mode. The imaging parameter values are passed to scan converter 34. Scan converter 34 processes the parameter data by performing a translation from scan sequence format to display format. The translation includes performing interpolation operations on the parameter data to create display pixel data in the display format.

The scan converted pixel data is sent to display processor 36 to perform any final spatial or temporal filtering of the scan converted pixel data, to apply grayscale or color to the scan converted pixel data, and to convert the digital pixel data to analog data for display on monitor 38. The user interface 40 interacts with the control processor 28 based on the data displayed on monitor 38.

Figure 2:
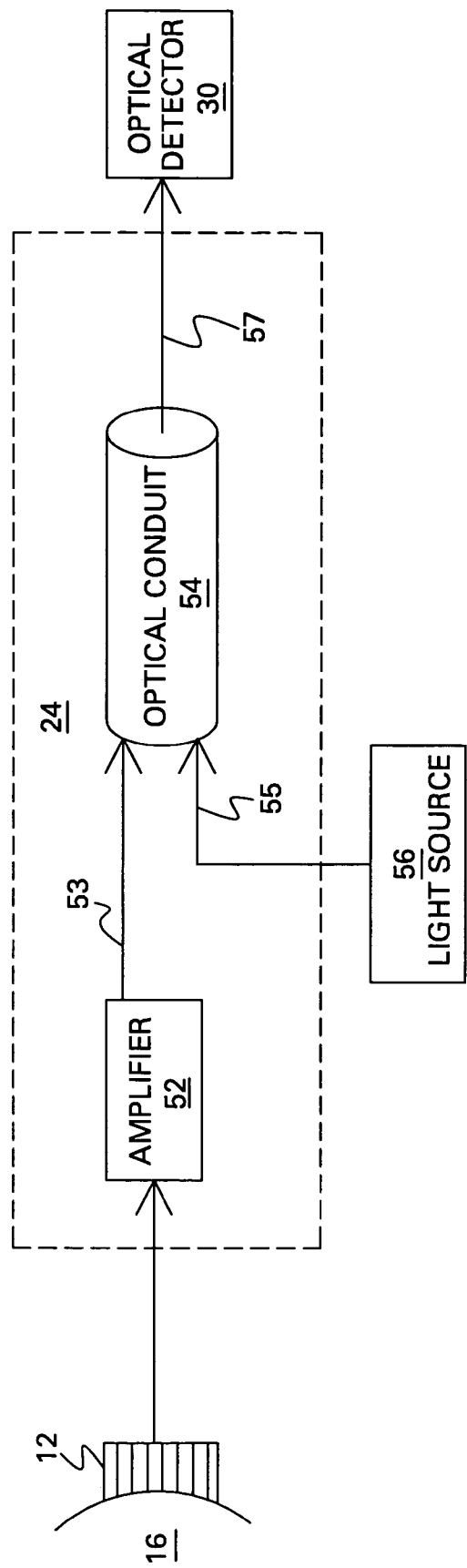
FIG. 2 is a block diagram of one embodiment of an acquisition subsystem implemented according to one aspect of the invention.

As described above, the received electrical signals are routed through receiver 24 to the processing subsystem 14. FIG. 2 is a block diagram of an embodiment of receiver 24 implemented according to one aspect of the invention. Receiver 24 comprises amplifier 52, light source 56 and optical detector 30. The light source is coupled to the optical detector via an optical conduit 54. Each component of the receiver is described in further detail below.

Amplifier 52 is configured for amplifying the received analog electrical signals from the ultrasound probe 12. In one embodiment, the received electrical signals are range from micro volts to milli volts and are amplified to a few volts. In one embodiment, the amplifier is implemented using analog devices such as transistors. Optical conduit 54 receives the amplified analog electrical signals from amplifier 52 on line 53. The optical conduit also receives continuous wave light generated by light source 56 on line 55. The optical conduit is configured for transforming the analog electrical signals to optically modulated analog signals and is transmitted to the optical detector 30 on line 57. Transmitting the optically modulated analog signals is advantageous because it eliminates the need for an analog to digital converter in the probe. The presence of the analog to digital converter in typical probe systems results in higher power requirements. In addition, the probe size is increased due to the addition of the analog to digital converter.

Optical detector 30 is configured to convert the optically modulated analog signals to corresponding electrical signals. The electrical signals are then transmitted to the processing subsystem for further signal processing. In one embodiment, the optical conduit comprises a fiber optic cable. In a further embodiment, the fiber optic cable comprises an optical waveguide and a plurality of optical fibers. As described above, the optical conduit is configured for transforming the electric signals to optical signals. The transformation is accomplished by using electro-optic modulators as illustrated in FIG. 3.

Figure 3:
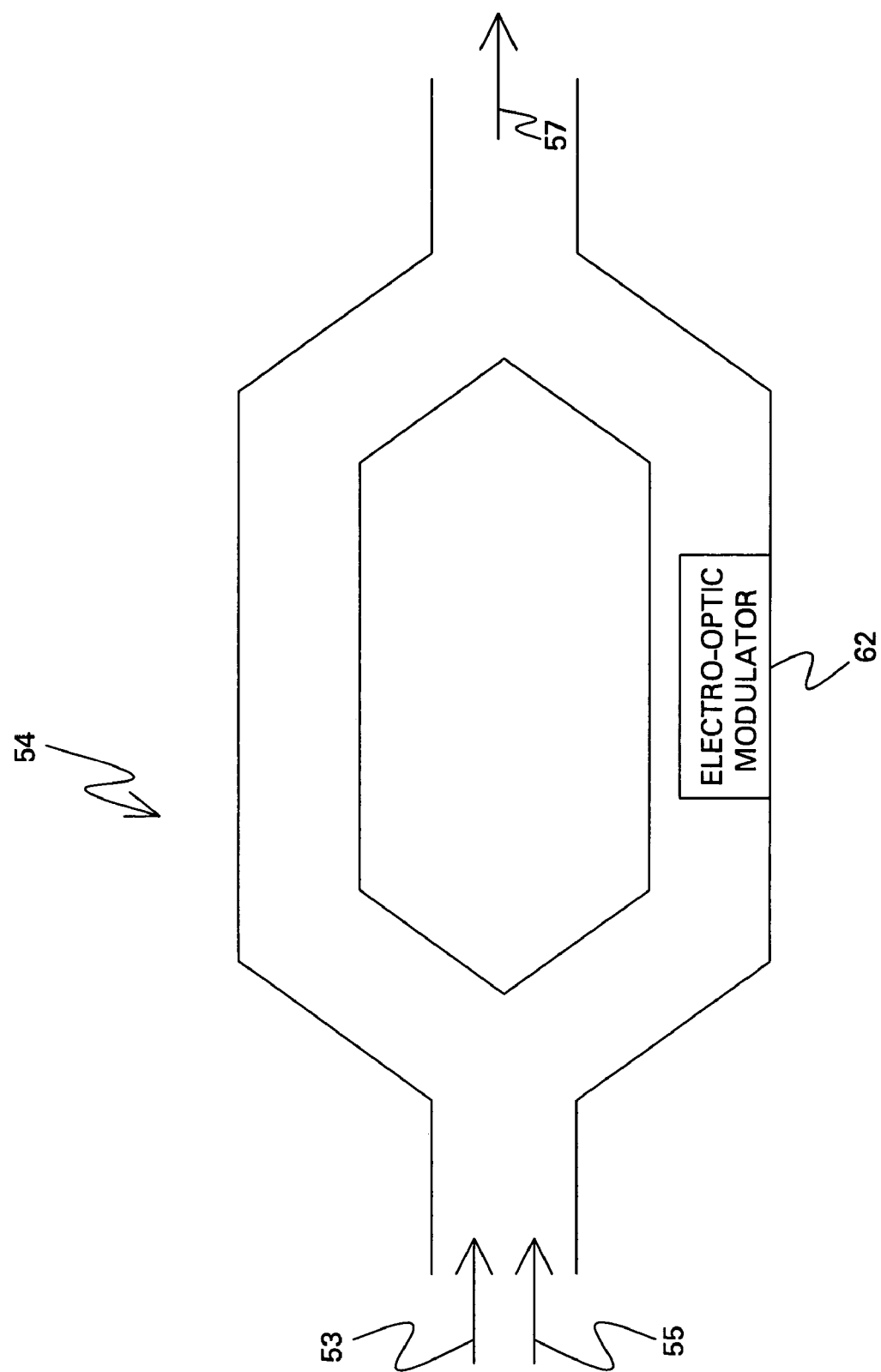
FIG. 3 is a block diagram of one embodiment of a modulator implemented according to one aspect of the invention.

FIG. 3 is a block diagram illustrating an optical waveguide using an electro-optic modulator implemented according to one aspect of the invention. Optical waveguide 54 receives the electrical signals from the ultrasound probe 12 as well as continuous wave light from light source 56 as inputs. Electro-optic modulator 62 is configured for modulating the continuous wave light with the electrical signals received from the ultrasound probe to generate the optically modulated analog signals shown by reference numeral 57.

Figure 4:
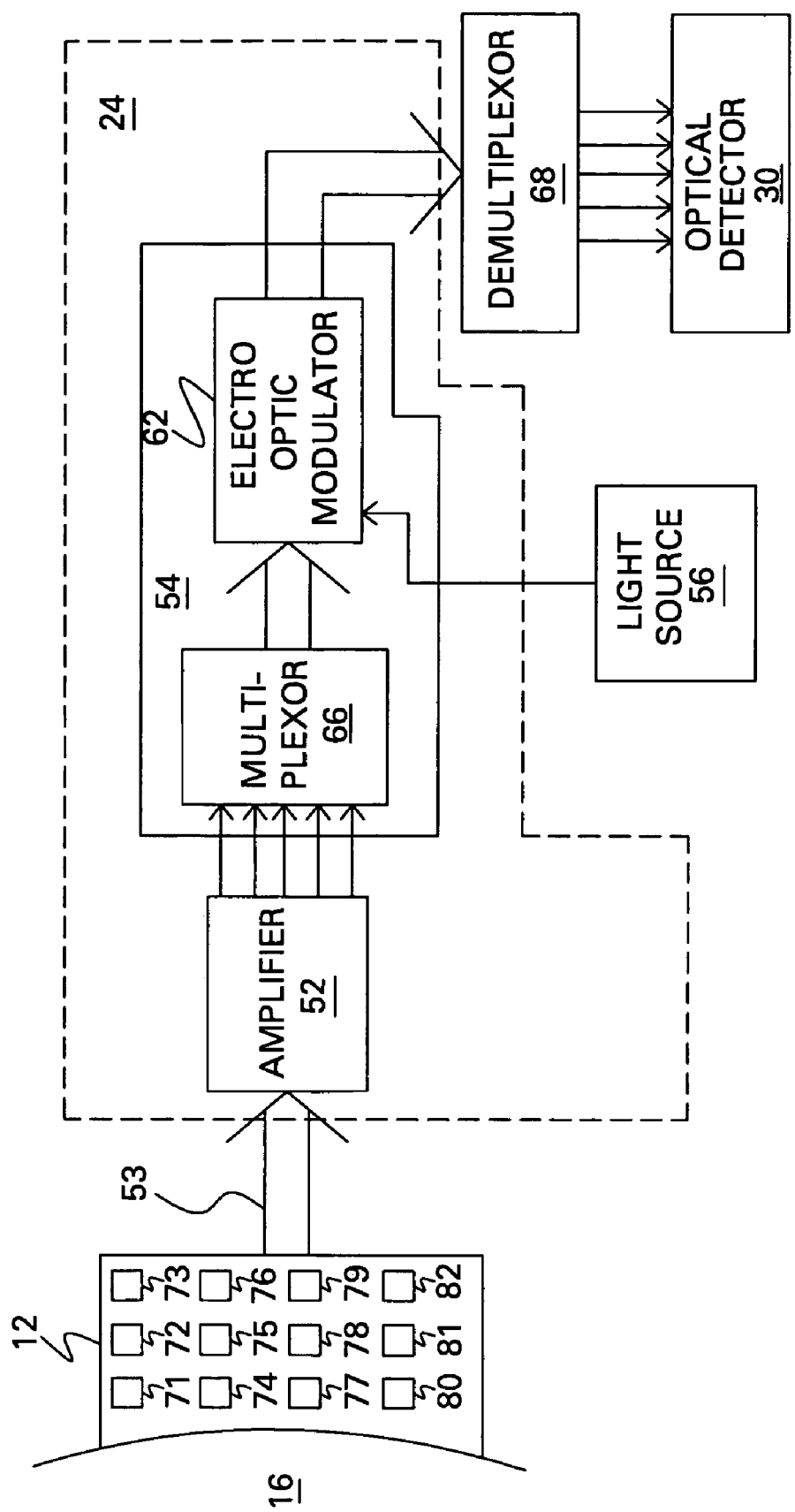
FIG. 4 is a block diagram of an embodiment of a receiver implemented according to one aspect of the invention.

The optically modulated analog signals are then transmitted to optical detector and the processing subsystem for further processing. The electro-optic modulator is implemented using polymer materials. Polymer material is best suited for electro-optic modulators because of compactness and reduced input power requirements. In addition, polymer modulators are lossless devices and hence do not generate substantial amount of heat in the ultrasound system. In a further embodiment of the invention as illustrated in FIG. 4, a multiplexer 66 is used in receiver 24. As described with reference to FIG. 1, ultrasound probe 12 comprises a plurality of transducer elements 71-82, each transducer configured to generate an electrical signal representative of the backscattered waves. The electrical signals are collectively shown by reference numeral 53.

Multiplexer 66 is configured for coupling the electro-optic modulator 62 and a corresponding set of transducers and conducting the electrical signals from the set of transducers to the electro-optic modulator. For example, in one embodiment, multiplexer 66 couples transducers 71-76 to electro-optic modulator 62. In a further embodiment, multiplexer 66 comprise a plurality of multiplexers and optical conduit 54 comprises a plurality of electro-optic modulators. In such an arrangement, the multiplexers are configured to couple a set of transducers and a corresponding set of electro-optic modulators. In addition, optical signals can be multiplexed by using wavelength, allowing many electrical signals to be transmitted on a single optical fiber, which typically results in better image resolution without having to increase cable requirements.

Demultiplexer 68 is configured demultiplexing the optically modulated analog signals received from the electro-optic modulators. The de-multiplexed optically modulated analog signals are transmitted to optical detector 30. Optical detector 30 comprises a plurality of photosensitive devices. Each demultiplexed optically modulated analog signal generated by the de-multiplexer is coupled to a respective photosensitive device in the optical detector. The photosensitive devices in turn are configured to convert the optically modulated analog signals to electrical signals. In a further embodiment, de-multiplexer 68 comprises a plurality of de-multiplexers and optical conduit 54 comprises a plurality of electro-optic modulators.

Figure 5:
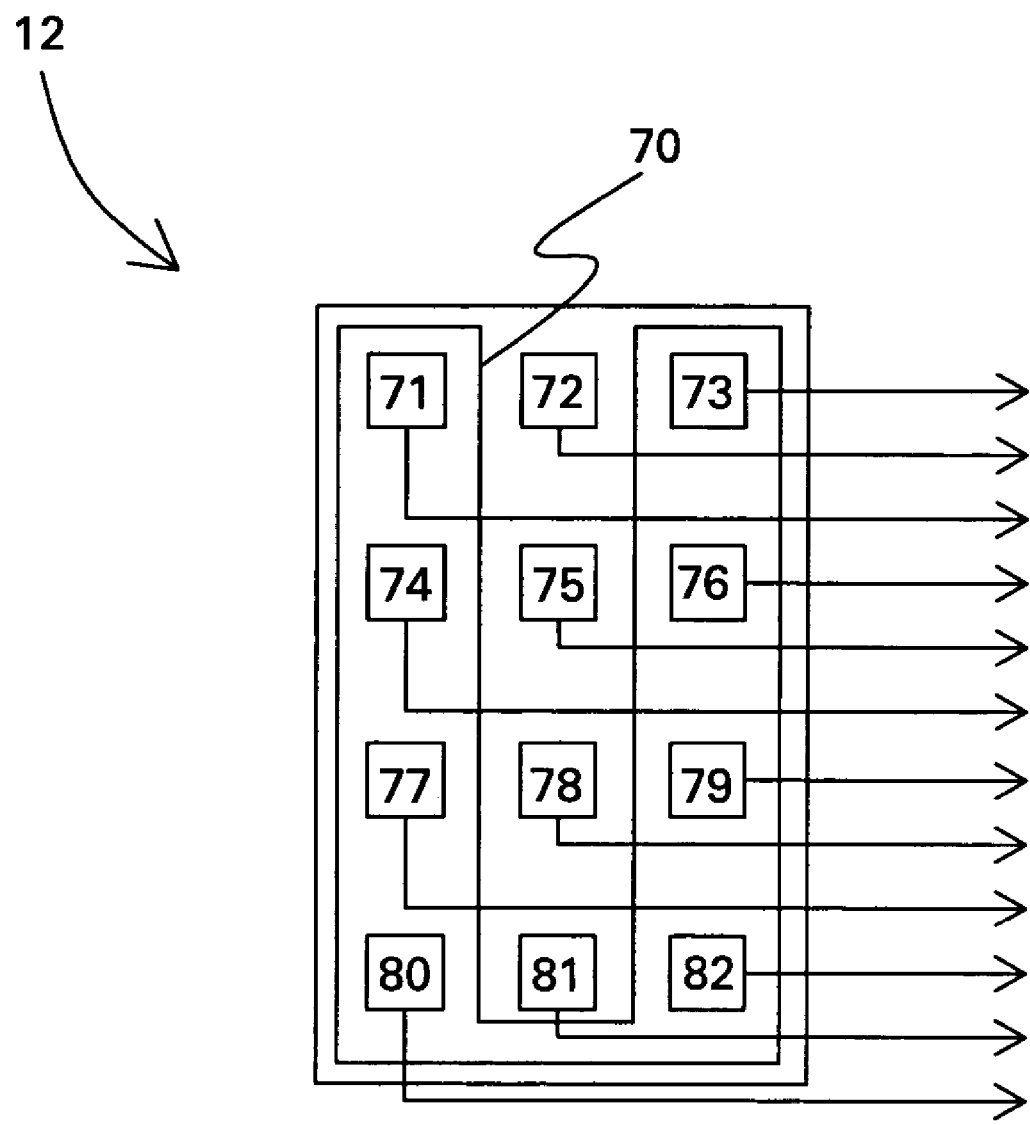
FIG. 5 is a block diagram of an ultrasound probe implemented according to one aspect of the invention.

In a further embodiment, illustrated in FIG. 5, the ultrasound probe 12 of the ultrasound system further comprises cooling line 70 configured for maintaining a probe temperature. In an alternate embodiment, the ultrasound probe comprises a plurality of cooling lines configured for maintaining a probe temperature.

The ultrasound probe illustrated in FIG. 5 comprises transducer elements 71-82. The ultrasound probe additionally comprises electronic and optical components 24 as shown in FIG. 4. The cooling line 70 is configured for absorbing the heat generated by the transducer elements and electronic components. In one embodiment, the cooling line comprises a coolant. Examples of the coolant used include water, water/alcohol mixtures, perfluorinated liquids, and combinations thereof. The cooling fluid absorbs heat from the probe through a heat exchanger. The heated fluid is returned back to the system where the heat is removed from the fluid by means of a second heat exchanger. The subsequently cooled fluid is pumped back to the probe where this process cycle repeats.

Figure 6:
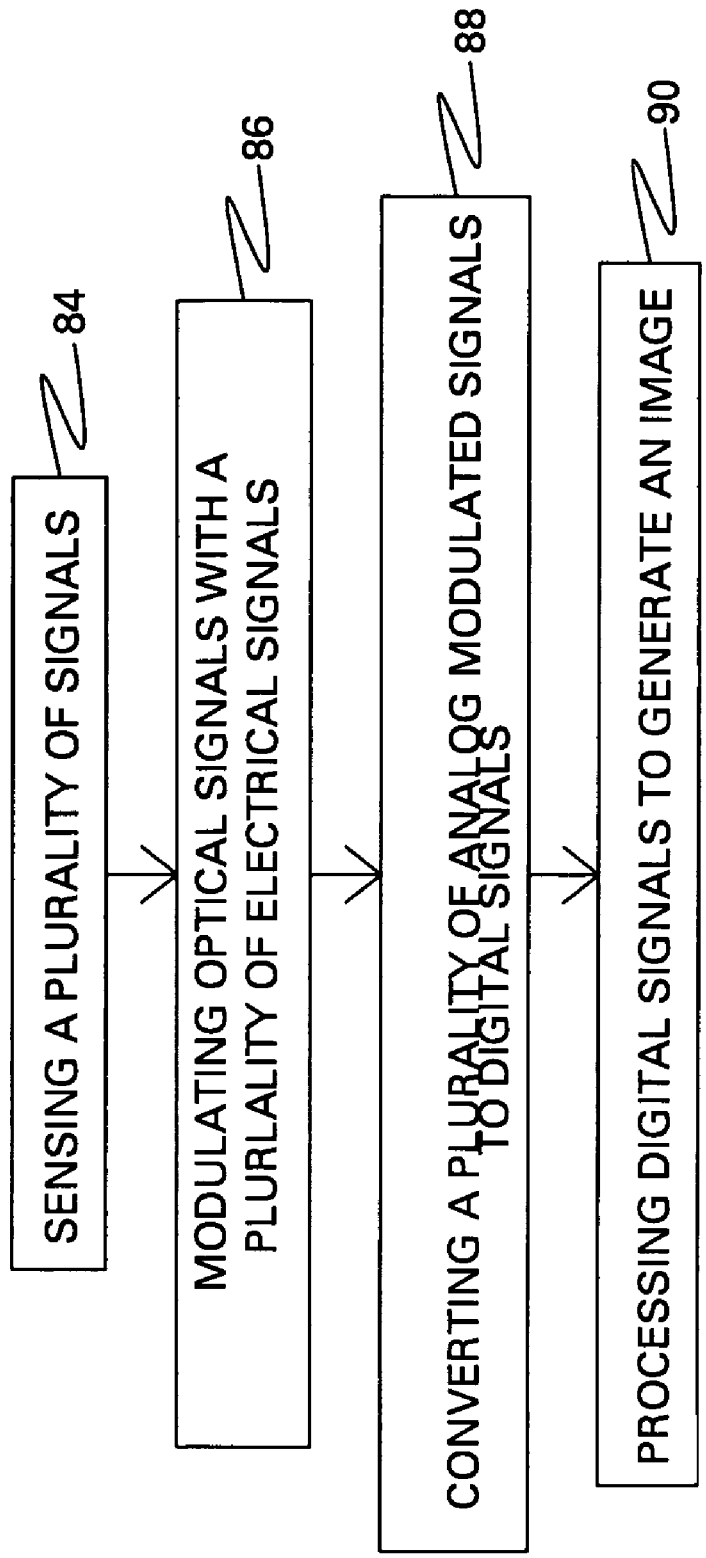
FIG. 6 is a flow chart illustrating one method by which the invention is implemented.

The above described invention is illustrated as steps in a flow chart. FIG. 6 is a flow chart illustrating the various steps in the invention. Each step is described in further detail below.

In step 84, a plurality of signals is sensed and corresponding electrical signals are generated. In one embodiment, the plurality of signals comprises ultrasound signals. The ultrasound signals are sensed using an ultrasound probe. In one embodiment, the ultrasound probe comprises piezoelectric transducers.

In step 86, the electrical signals are modulated with a plurality of optical signals to generate a corresponding plurality of optically modulated analog signals. In one embodiment, the electrical signals are modulated using electro-optic modulators. In a more specific embodiment, the electro-optic modulators comprise polymer electro-optic modulators. In a further specific embodiment, the electro-optic modulator comprises Mach Zehnder electro-optic modulators.

In step 88, the plurality of optically modulated analog signals is converted to a corresponding plurality of digital signals. In step 90, the plurality of digital signals is processed to generate the image.

The previously described embodiments of the present invention have many advantages, including providing a light ultrasound probe by using optical fibers which provides easier maneuverability. In addition, the temperature of the ultrasound probe is also maintained by incorporating a cooling line in the design.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An ultrasound system comprising:
   an ultrasound probe comprising a plurality of transducer elements configured for sensing ultrasound signals and converting the ultrasound signals to analog electrical signals, the ultrasound probe configured for transmitting the analog electrical signals;
   an optical conduit comprising an electro-optic modulator configured for
   (a) receiving the analog electrical signals,
   (b) receiving optical signals from a light source, and
   (c) modulating the optical signals with the analog electrical signals;
   wherein the optical conduit is configured for transmitting the modulated optical signals to an optical detector.

2. The ultrasound system of claim 1, wherein the electro-optic modulator comprises a plurality of electro-optic modulators.

3. The ultrasound system of claim 2, wherein the electro-optic modulators each comprise a polymer material or silicon.

4. The ultrasound system of claim 2, wherein the ultrasound probe further comprises:
   an amplifier configured for amplifying the analog electrical signals.

5. The ultrasound system of claim 2, wherein the plurality of transducer elements comprises a plurality of sets of transducer elements and wherein the optical conduit further comprises:
   a plurality of multiplexers, each configured for coupling a corresponding one of the electro-optic modulators and a corresponding set of the transducer elements and conducting electrical signals of a selected one set of transducer elements to the corresponding one of the electro-optic modulators.

6. The ultrasound system of claim 5, wherein the ultrasound system further comprises a plurality of demultiplexers configured for demultiplexing the optically modulated analog signals received from the electro-optic modulators.

7. The ultrasound system of claim 1, wherein the ultrasound probe further comprises a plurality of cooling lines configured for maintaining a probe temperature.

8. The ultrasound system of claim 1, wherein the light source comprises a laser source.

9. The ultrasound system of claim 8, further comprising the optical detector, wherein the optical detector is configured for converting the optically modulated analog signals to corresponding digital signals.

10. A method for generating an image, the method comprising:

sensing ultrasound signals, converting the ultrasound signals to analog electrical signals;

receiving optical signals from a light source;

modulating the optical signals with the analog electrical signals to generate a corresponding plurality of optically modulated analog signals;

converting the plurality of optically modulated analog signals to a corresponding plurality of digital signals; and processing the plurality of digital signals to generate the image.

11. The method of claim 10, wherein the plurality of signals comprise ultrasound signals.

12. The method of claim 11, wherein sensing further comprises amplifying the electrical signals.

* * * * *